United States Patent
Dornieden

(10) Patent No.: US 9,011,553 B2
(45) Date of Patent: Apr. 21, 2015

(54) FLEXIBLE LAMINATE AND METHOD FOR THE PRODUCTION THEREOF

(71) Applicant: Otto Bock Healthcare GmbH, Duderstadt (DE)

(72) Inventor: Dionys Dornieden, Neuendorf (DE)

(73) Assignee: Otto Bock Healthcare GmbH, Duderstadt (DE)

(*) Notice: Subject to any disclaimer, the term of this patent is extended or adjusted under 35 U.S.C. 154(b) by 43 days.

(21) Appl. No.: 13/893,988

(22) Filed: May 14, 2013

(65) Prior Publication Data
US 2013/0309506 A1    Nov. 21, 2013

(30) Foreign Application Priority Data
May 15, 2012 (DE) .......... 10 2012 010 825

(51) Int. Cl.
| | |
|---|---|
| B32B 3/30 | (2006.01) |
| B32B 7/12 | (2006.01) |
| A61L 27/18 | (2006.01) |
| C08L 75/04 | (2006.01) |
| A61F 2/78 | (2006.01) |
| B32B 7/04 | (2006.01) |
| B32B 25/08 | (2006.01) |
| B32B 25/20 | (2006.01) |
| B32B 27/08 | (2006.01) |
| B32B 27/28 | (2006.01) |
| B32B 27/40 | (2006.01) |
| B32B 37/12 | (2006.01) |
| C08L 65/04 | (2006.01) |

(52) U.S. Cl.
CPC ........... *B32B 37/1284* (2013.01); *A61F 2/7812* (2013.01); *B32B 3/30* (2013.01); *B32B 7/04* (2013.01); *B32B 7/12* (2013.01); *B32B 25/08* (2013.01); *B32B 25/20* (2013.01); *B32B 27/08* (2013.01); *B32B 27/28* (2013.01); *B32B 27/283* (2013.01); *B32B 27/40* (2013.01); *B32B 2255/10* (2013.01); *B32B 2274/00* (2013.01); *B32B 2535/00* (2013.01); *C08G 2261/3424* (2013.01); *C08L 65/04* (2013.01); *Y10S 623/901* (2013.01)

(58) Field of Classification Search
USPC .......................... 623/901, 36; 428/424.8, 480
See application file for complete search history.

(56) References Cited

U.S. PATENT DOCUMENTS

| | | | |
|---|---|---|---|
| 5,654,084 A | 8/1997 | Egert | |
| 6,586,048 B2 | 7/2003 | Welch, Jr. et al. | |
| 6,806,347 B2 * | 10/2004 | Hogge et al. | 528/396 |
| 2005/0043581 A1 | 2/2005 | Ling et al. | |
| 2008/0057274 A1 * | 3/2008 | Hagiwara et al. | 428/172 |

(Continued)

FOREIGN PATENT DOCUMENTS

| | | |
|---|---|---|
| DE | 2617678 A1 | 11/1976 |
| DE | 102008063818 A1 | 6/2010 |

(Continued)

*Primary Examiner* — Thao T. Tran
(74) *Attorney, Agent, or Firm* — Holland & Hart

(57) ABSTRACT

A flexible laminate formed from at least a first layer comprising a first flexible elastomer and a second layer comprising a second flexible elastomer, which are connected to one another by an intermediate layer. The intermediate layer comprises parylene and is applied to the first layer such that the intermediate layer has an irregular surface with irregularities. The second flexible elastomer or an adhesive connected to the second layer is applied in liquid form to the intermediate layer such that the irregularities the intermediate layer are at least partially filled.

16 Claims, 2 Drawing Sheets

(56) References Cited

U.S. PATENT DOCUMENTS

| | | | |
|---|---|---|---|
| 2008/0305143 A1 | 12/2008 | Chen et al. | |
| 2009/0240344 A1* | 9/2009 | Colvin et al. | 623/36 |
| 2010/0174239 A1 | 7/2010 | Yodfat et al. | |
| 2011/0320011 A1 | 12/2011 | Anhalt | |
| 2012/0123560 A1* | 5/2012 | Chen | 623/36 |

FOREIGN PATENT DOCUMENTS

| | | |
|---|---|---|
| EP | 0764681 B1 | 7/1999 |
| EP | 1806224 A1 | 7/2007 |
| GB | 1545468 | 5/1979 |
| WO | 2007025059 A1 | 3/2007 |
| WO | 2012005614 A1 | 1/2012 |
| WO | 2012140262 A1 | 10/2012 |

* cited by examiner

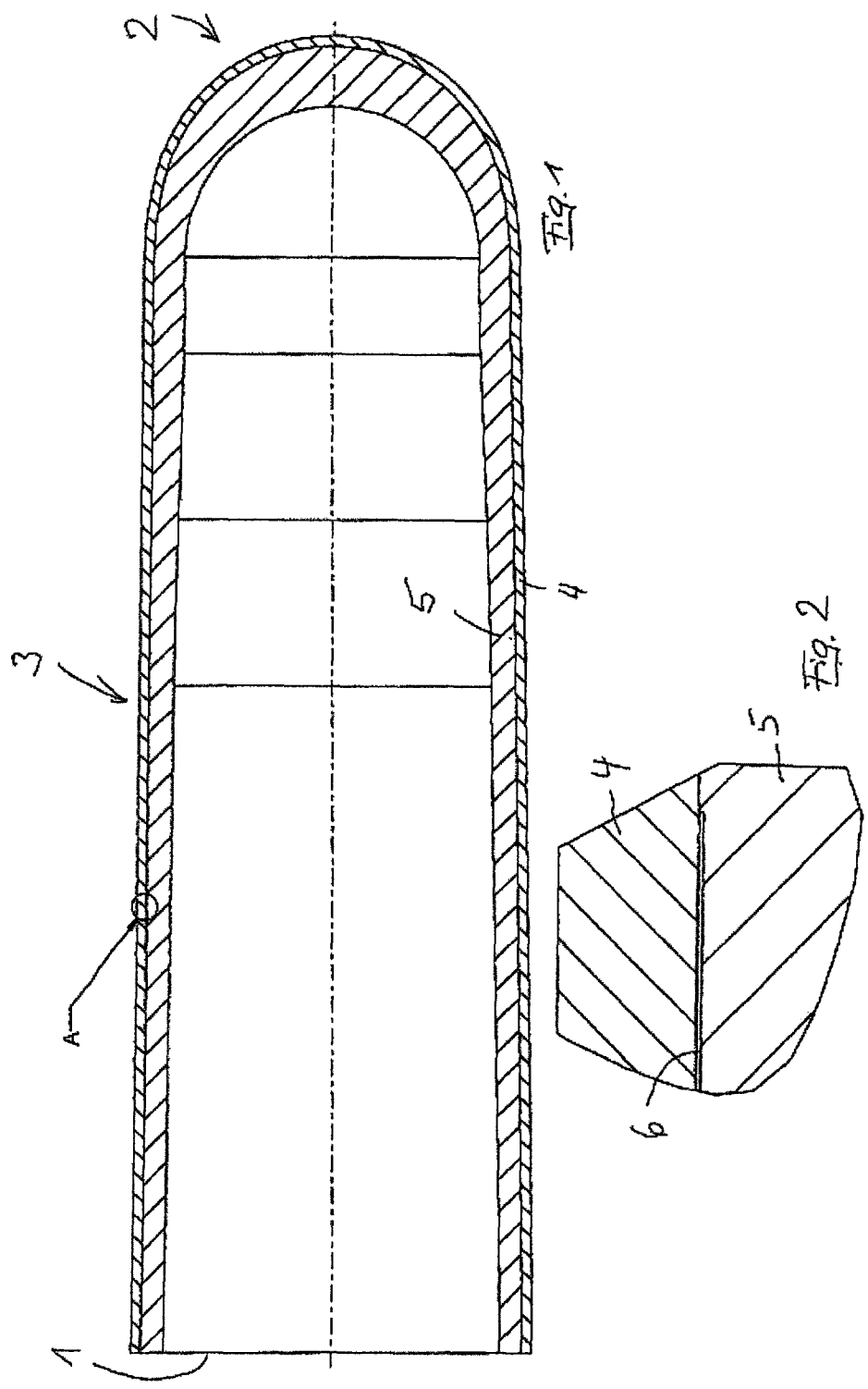

FLEXIBLE LAMINATE AND METHOD FOR THE PRODUCTION THEREOF

CROSS-REFERENCE TO RELATED APPLICATION

This application claims priority to German Patent Application No. 102012010825.7, filed 15 May 2012, now German Patent No. DE102012010825 issued 28 Mar. 2013 and entitled FLEXIBLE LAMINATE AND METHOD FOR THE PRODUCTION THEREOF, the disclosure of which is incorporated, in its entirety, by reference.

TECHNICAL FIELD

The invention relates to a flexible laminate, formed by at least a first layer of a first flexible elastomer and a second layer of a second flexible elastomer, which are connected to one another by an intermediate layer applied to the first layer.

The invention also relates to a method for producing a flexible laminate from at least a first layer of a first flexible elastomer and a second layer of a second flexible elastomer, which are connected to one another by an intermediate layer applied to the first layer.

BACKGROUND

It is known that certain elastic synthetic materials cannot be connected to one another unproblematically. For example, it is not possible to connect a silicone layer and a polyurethane layer to one another directly or with adhesives. The coating of silicone is therefore always problematic.

There is a similar problem with the coating of thermoplastic elastomers, as are formed, for example, on the basis of styrene-isoprene-butadiene block copolymers or styrene-ethylene/butylene copolymers. These thermoplastic elastomers (TPEs) may have a high oil content, making surface-area connection to other materials problematic.

US 2009/0240344 A1 discloses a connection of the materials by a textile intermediate layer that can be connected to both materials. However, the laminate formed loses flexibility as a result. In addition, the layer thickness is increased. It is also known from the same document to provide one of the layers with a textured surface, for example in the form of numerous hooks, in order in this way to achieve a mechanical anchoring of the layer of the other synthetic material that is subsequently poured on. Such a method is complex.

DE 26 17 678 A1 discloses producing a polymer composite material from two polymeric components, one of which is a vulcanized rubber and the other is a different vulcanized rubber or a plastic. The connection of the polymeric components is established by a particulate binder layer that predominantly contains particles of carbon and/or a silicon compound being provided at the interface of the components. This layer is penetrated by both components.

DE 10 2008 063 818 A1 discloses providing an orthopedic pad of a fluid-filled elastomer, an elastomer gel, a plasticized thermoplastic or a polyurethane with a friction-reducing layer by subjecting the fully polymerized pad at least to a pretreatment step in which volatile constituents are extracted from the surface and the pad is subsequently coated with a non-polar polymer coating that increases the surface slip. The polymeric coating material may in this case be poly(para-xylylene) (common trivial name: parylene).

SUMMARY

The present invention is based on the object of making possible a surface-area connection of a first flexible elastomer to a second flexible elastomer to form a flexible laminate in which the flexibility is not noticeably impaired by the intermediate layer and no significant increase in the thickness of the laminate is necessary due to the intermediate layer.

To achieve this object, the flexible laminate of the type mentioned at the beginning is characterized in that the intermediate layer is a parylene layer with an irregular surface and that the second elastomer or an adhesive connected to the second layer at least partially fills the irregularities of the surface of the parylene layer.

The object is also achieved by a method of the type mentioned at the beginning, in that a parylene layer is applied to the first layer, so that the parylene layer is applied by chemical vapor deposition (CVD) such that the parylene layer has a surface roughness caused by an irregular surface and that the second elastomer or an adhesive connected to the second layer is applied in liquid form to the parylene layer such that the irregularities of the surface of the parylene layer are at least partially filled.

According to the invention, consequently a parylene layer that acts as an adhesion promoter is used. This is surprising because parylene is known as a friction-reducing material, which consequently allows only low adhesion on its surface.

However, the present invention is based on the realization that the parylene layer can form an irregular surface, in particular if it is applied by the CVD process (Chemical Vapor Deposition). The surfaces thus formed are not countered by a reduction in the coefficient of friction by the parylene area, but make it possible for a liquid polymer to fill the irregularities, so that the second elastomer in liquid form or an adhesive in liquid form that is connected to the second layer of the second elastomer can interlock with the surface of the parylene layer, and thus bring about a predominantly mechanical connection of the second layer to the first layer. The irregularities may comprise undercuts, which are conducive to the interlocking of the materials to one another. The undercuts may in this case also be formed by pores which increase in size from the surface to the interior of the material. When the parylene layer is applied by the CVD process, a surface with an irregular, grid-like structure of crossing furrows, which likewise bring about, or are at least conducive to, the mechanical connection of the layers to one another, is additionally produced.

It has been found that first elastomers that are difficult to coat can be stably coated with parylene, in particular if the parylene layer is applied to the first layer by CVD. This allows silicones and thermoplastic elastomers in particular to be directly coated with a parylene layer, the parylene layer, because of its irregularity, at least also establishing a mechanical connection to the second elastomer, or the adhesive connected to it, when the second elastomer or the adhesive has penetrated into the irregularities of the parylene layer.

It is therefore necessary that the second elastomer or the adhesive establishing the connection to the second elastomer is applied in liquid form to the first elastomer coated with the parylene layer, so that the penetration into the irregularities is made possible and the second elastomer or the adhesive at least partially fills the irregularities. An interlocking connection thereby comes about in particular if the irregularities have undercuts, for example in the form of pore-like interspaces.

The first elastomer is preferably a silicone or a thermoplastic elastomer. This first elastomer is coated with the parylene layer, preferably by CVD. As a result, the first elastomer can be connected to a second elastomer.

Polyurethane or a thermoplastic elastomer come into consideration in particular as the second elastomer, silicone being preferred in particular as the first elastomer when a thermoplastic elastomer is used as the second elastomer. In particular when a thermoplastic elastomer is used as the second elastomer, it may be advisable likewise to coat the second elastomer with a parylene layer, preferably by CVD, and then to connect the coated first elastomer and the coated second elastomer by a suitable adhesive, in particular polyurethane adhesive.

The parylene layer applied to the first layer preferably has a thickness of between 0.4 and 5 µm, more preferably between 0.7 and 4 µm, in particular 0.7 and 2 µm. In this case, the parylene layer in its thin version may be applied in a single application by means of CVD, while for greater layer thicknesses a double or triple coating is advisable. For the low layer thickness of 0.7 µm, in an exemplary embodiment an Rz value of 11.4 and a value for the average roughness Ra of 1.49 are obtained. In the case of a triple coating, a layer thickness of 1.56 µm has been obtained, leading to an Rz value of 30.9 and an Ra value of 3.67.

In the preferred layer thickness range, the elasticity of the two layers of elastomers is not noticeably reduced by the intermediate layer. This also applies if an adhesive, which is preferably produced on a polyurethane basis, is used for the connection by the second elastomer to the first elastomer coated by the parylene layer.

As a parylene (poly(para-xylylene)), the parylene N comes into consideration in particular as an adhesion promoter according to the invention. Tests have shown that the variants parylene F and parylene C can also be used almost equivalently.

The flexible laminate according to the invention may be used as a flat material or as a preformed material. The connection of the two elastomers to one another to form the flexible laminate offers the advantage that different advantages of the two elastomers can be used in one laminate. For instance, the good adaptability of a polyurethane layer can be combined with the good resilient properties and the relative insensitivity of a silicone layer. In a similar way, the good skin compatibility of a thermoplastic elastomer, which has a high white oil content, can be combined with the mechanical stability and tear resistance of the silicone layer. Preferred combinations are therefore silicone as the first elastomer with polyurethane as the second elastomer and TPE as the first elastomer with silicone as the second elastomer.

A particularly preferred use of the flexible laminate according to the invention is the use as a liner for a prosthetic that takes the place of an amputated limb. The connection of the prosthesis in this case takes place by way of a prosthetic socket, which comprises an amputation stump, for example on a lower leg or on an upper leg in the case of a leg prosthesis. The liner is applied to the amputation stump, for example rolled up because of its elasticity, in order in this way to lie firmly against the amputation stump and adapt to the irregularities of the amputation stump. Consequently, the liner is, for example, directly on the skin of the amputation stump and should therefore have a good skin-compatible inner layer. This may consist, for example, of polyurethane or of TPE. If, as is possible in the case of the flexible laminate according to the invention, the liner has an outer layer of silicone, for example, the silicone offers a mechanically stable outer layer of the liner but additionally has good resilient properties, in order in this way to press the cushioning inner layer of polyurethane or TPE against the amputation stump, whereby the inner layer adapts to the irregularities of the surface of the amputation stump.

In some cases it may also be advisable to utilize the cushioning properties of the polyurethane or the TPE with the resilient properties of the silicone by the skin-friendly and easy-to-clean silicone forming the inner layer of the liner and the cushioning elastomer layer of polyurethane or TPE forming the outer layer. In this case, it may incidentally be advisable to provide the outer layer with a sliding layer, for example by a textile layer or a parylene coating, which then does not act according to the invention as an adhesion promoter but—as known in the prior art—as an sliding layer. The sliding layer may, for example, facilitate the introduction of the amputation stump provided with the liner into the prosthetic socket or the removal of the amputation stump from the prosthetic socket.

Thermoplastic elastomers, which are generally SEBS-(styrene-ethylene/butylene-styrene) or SIBS-(styrene-isoprene/butadiene-styrene) based thermoplastic elastomers, in particular styrene-isoprene-butadiene block copolymers and styrene-ethylene/butylene copolymers, are preferred for this application. Such TPEs that come into consideration are, for example, Evoprene-TPE compositions from AlphaGary Ltd., United Kingdom, polymers of the series SEBS G from KRATON Polymers GBH, Germany, and Septon 4040 from Kuraray Europe GmbH, Germany.

An exemplary embodiment of the flexible laminate according to the invention in the form of a liner is represented in the drawing, in which:

BRIEF DESCRIPTION OF THE DRAWINGS

FIG. 1 shows a longitudinal section through a liner of a flexible laminate according to the invention;

FIG. 2 shows an enlarged detail of a longitudinal section for a variant of the liner according to FIG. 1;

DETAILED DESCRIPTION

Figure 3:
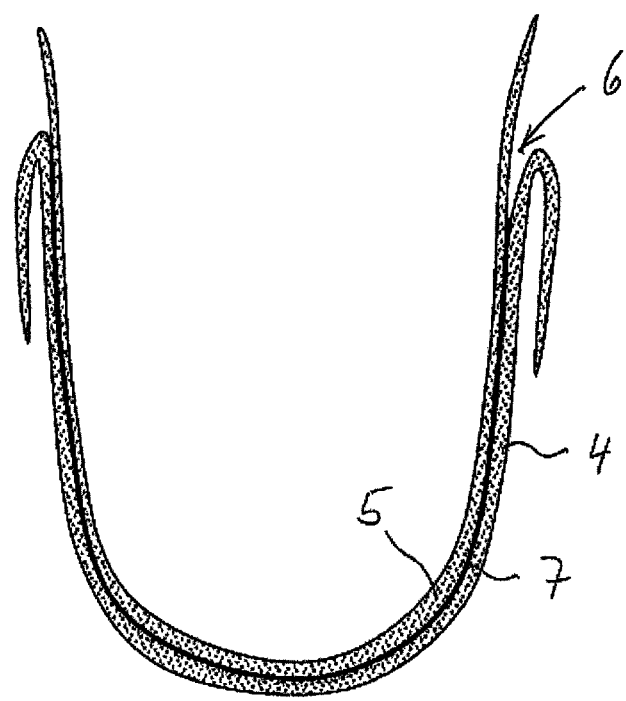
FIG. 3 shows a longitudinal section through a liner according to FIG. 2.

The liner represented in FIG. 1 has a proximal open end 1, a distal closed end 2 and a middle piece 3, extending substantially cylindrically or approximately conically between the ends 1, 2.

The liner consists of a first, outer layer 4 of a first elastomer, for example silicone, and of a second, inner liner 5 of a second, skin-friendly elastomer, for example polyurethane. It is evident that the second layer 5 increases in thickness toward the distal end 2, in order to improve the cushioning of the amputation stump toward the distal end and ensure greater comfort.

The first layer 4 and the second layer 5 may be connected to one another by their surface area over the entire length of the liner.

The surface-area connection may in this case completely or only partially comprise the surfaces of the first layer and the second layer lying against one another. For instance, it may be adequate to connect the first layer 4 and the second layer 5 only partially to one another, for example in the form of strips or connecting points distributed over the surface area. This variant is obvious in particular when an adhesive is used.

The surface-area connection is made possible by the first layer 4 having been coated with a parylene layer (not represented any more specifically), having irregular surfaces, in particular by the CVD process, as an intermediate layer. When the parylene layer has been applied by the CVD process, it has a sinter-like structure with pore-like interspaces, widening toward the interior of the material, which act as undercuts. The second layer 5, for example of polyurethane, may then be applied to the coated first layer directly, i.e.

without adhesive, if the second layer is first formed in a mold, so that the second elastomer of the second layer 5 in liquid form is brought into contact with the inner side, formed by the parylene layer, of the first layer 4. This allows the liquid material of the second elastomer of the second layer 5 to penetrate partially into the irregularity of the applied parylene layer, and thus provide a solid connection between the second layer 5 and the first layer 4.

However, it is also possible to pre-produce the second layer 5 in a form that complements the first layer 4 and adhesively incorporate it in the formed state into the first layer 4. In this case, an adhesive is used, on the one hand bringing about a solid connection to the second elastomer of the second layer 5 and on the other hand penetrating in the liquid state into the pores of the parylene layer on the inner side of the first layer 4.

In particular in the case of the described adhesive bond of the second layer 5 to the first layer 4, it is possible to realize the variant represented in FIGS. 2 and 3, in which the adhesive bond takes place by their surface area over the distal end 2 and the greatest part of the shell region 3, but toward the proximal end is ended in the region A in FIG. 1, so that toward the proximal end the first layer 4 as the outer layer and the second layer 5 as the inner layer are not connected to one another, as can be seen from the interspace 6 between the outer first layer 4 and the inner second layer 5 in the enlarged representation of FIG. 2. As FIG. 3 illustrates, it is possible to fold over the outer first layer 4 outwardly in the region in which the two layers 4, 5 are not connected to one another by their surface area, that is to say in the region of the interspace 6, in order, for example, to bring about a sealing of the proximal periphery of the prosthetic socket (not represented), if it is intended to produce between the liner and the prosthetic socket a negative pressure by which the prosthetic socket is securely held on the amputation stump provided with the liner during use.

FIG. 3 illustrates that the connection between the layers 4 and 5 may take place by means of an adhesive 7.

It has been found that the parylene intermediate layer according to the invention allows even elastomers that cannot otherwise be connected to one another to be solidly connected to one another and to withstand shearing forces that way lie between 0.2 and 1.4 N/mm. This connecting force is sufficient by far for use as a liner, but cannot be achieved without the parylene intermediate layer according to the invention when connecting material pairings such as silicone-polyurethane, TPE-silicone and TPE-polyurethane, because no noticeable adhesive effect is achieved with these material pairings.

What is claimed is:

1. A prosthetic liner having a flexible laminate that is comprised:
   a first layer of a first flexible elastomer;
   a second layer of a second flexible elastomer;
   an intermediate layer applied to the first layer and operable to connect the first and second layers together, wherein the intermediate layer is a parylene layer with an irregular surface, and the second elastomer or an adhesive connected to the second layer at least partially fills the irregularities of the surface of the parylene layer.

2. The prosthetic liner according to claim 1, wherein the parylene layer is applied to the first layer by chemical vapor deposition (CVD).

3. The prosthetic liner according to claim 1, wherein the first flexible elastomer comprises silicone or a thermoplastic elastomer (TPE).

4. The prosthetic liner according to claim 1, wherein the second flexible elastomer comprises polyurethane or a thermoplastic elastomer (TPE).

5. The prosthetic liner according to claim 1, wherein the second layer forms an inner layer of the prosthetic liner, the first layer covering an outer surface of the second layer.

6. A method for producing a prosthetic liner having a flexible laminate, the method comprising:
   providing at least a first layer of a first flexible elastomer, a second layer of a second flexible elastomer, and an intermediate layer, the intermediate layer comprising parylene;
   connecting the first and second layers to one another with the intermediate layer, wherein an intermediate layer is applied to the first layer such that the intermediate layer has a surface roughness caused by an irregular surface and the second elastomer or an adhesive connected to the second layer is applied in liquid form to the intermediate layer such that the irregularities of the surface of the intermediate layer are at least partially filled.

7. The method according to claim 6, wherein the first flexible elastomer comprises a silicone or a thermoplastic elastomer (TPE).

8. The method according to claim 6 wherein the second flexible elastomer comprises a thermoplastic elastomer (TPE) or a polyurethane comprises.

9. A prosthetic liner having a flexible laminate that is comprised of:
   a first layer comprising a first flexible elastomer;
   a second layer comprising a second flexible elastomer;
   an intermediate layer comprising parylene and having an irregular surface with irregularities, the intermediate layer connecting the first layer to the second layer;
   wherein the second flexible elastomer or an adhesive applied to the second layer at least partially fills the irregularities of the intermediate layer;
   wherein the flexible laminate comprises a prosthetic liner.

10. The prosthetic liner according to claim 9, wherein the intermediate layer is applied to the first layer by chemical vapor deposition (CVD).

11. The prosthetic liner according to claim 9, wherein the first flexible elastomer comprises silicone or a thermoplastic elastomer (TPE).

12. The prosthetic liner according to claim 9, wherein the second flexible elastomer comprises polyurethane or a thermoplastic elastomer (TPE).

13. The prosthetic liner according to claim 9, wherein the second layer forms an inner layer of the prosthetic liner, the first layer covering an outer surface of the second layer.

14. A method for producing a prosthetic liner having a flexible laminate, comprising:
   providing at least a first layer comprising a first flexible elastomer, a second layer comprising a second flexible elastomer, and an intermediate layer comprising parylene, the intermediate layer having an irregular surface with irregularities;
   applying the intermediate layer to the first layer;
   connecting the second layer to the intermediate layer, wherein the second flexible elastomer or an adhesive connected to the second layer is applied in liquid form to the irregular surface such that the irregularities are at least partially filled.

15. The method according to claim 14, wherein the first flexible elastomer comprises a silicone or a thermoplastic elastomer (TPE).

16. The method according to claim 14, wherein the second flexible elastomer comprises a thermoplastic elastomer (TPE) or a polyurethane.

\* \* \* \* \*